(12) United States Patent  
Crouse et al.

(10) Patent No.: US 11,035,788 B2  
(45) Date of Patent: Jun. 15, 2021

(54) TECHNOLOGIES FOR THE SELECTION AND PROCESSING OF PLANTS

(71) Applicant: TROPICANA PRODUCTS, INC., Bradenton, FL (US)

(72) Inventors: Jeremy Crouse, Bradenton, FL (US); Zhanfeng Xu, Bradenton, FL (US); Geovanne Ijpkemeule, Bradenton, FL (US); Johnny Casasnovas, Barrington, IL (US)

(73) Assignee: Tropicana Products, Inc., Bradenton, FL (US)

( * ) Notice: Subject to any disclaimer, the term of this patent is extended or adjusted under 35 U.S.C. 154(b) by 328 days.

(21) Appl. No.: 16/354,452

(22) Filed: Mar. 15, 2019

(65) Prior Publication Data

US 2020/0292446 A1 Sep. 17, 2020

(51) Int. Cl.
*G01J 3/00* (2006.01)
*G01N 21/359* (2014.01)
*G01J 3/10* (2006.01)
*G01N 21/84* (2006.01)
*G01N 33/02* (2006.01)

(Continued)

(52) U.S. Cl.
CPC ............ *G01N 21/359* (2013.01); *G01J 3/108* (2013.01); *G01N 21/84* (2013.01); *G01N 33/025* (2013.01); *G01N 33/03* (2013.01); *G01N 2021/1706* (2013.01); *G01N 2021/8466* (2013.01)

(58) Field of Classification Search
CPC .. G01N 21/314; G01N 21/33; G01N 21/3504; G01J 3/10; G01J 3/42
USPC .......................................................... 356/51
See application file for complete search history.

(56) References Cited

U.S. PATENT DOCUMENTS

| 6,293,189 B1 | 9/2001 | Evans et al. |
| 6,851,662 B2 | 2/2005 | Panigrahi et al. |
| 2018/0209901 A1 | 7/2018 | Schwartzer et al. |

FOREIGN PATENT DOCUMENTS

WO 01/69191 9/2001

OTHER PUBLICATIONS

Brown Int'l Corp., "Model 6100—Brown Oil Extractor," accessible on the Internet at: https://www.brown-intl.com/Brown/media/Brown-PDFs/MDL-BOE-NF-Brochure-8-1-18.pdf (publicly available prior to filing of the instant application).

(Continued)

*Primary Examiner* — Md M Rahman
(74) *Attorney, Agent, or Firm* — Barnes & Thornburg LLP (57) ABSTRACT

A method for sourcing plants includes performing nondestructive near-infrared (NIR) scans on selected plants, determining a predicted value of a characteristic for the selected plants based on evaluation of spectral data from the NIR scans against a characteristic model, and utilizing the predicted values for purchasing, processing, and/or financial forecasting. A method of sorting and processing plants includes determining a predicted value of a characteristic in gathered plants and determining a process to recover a primary product and/or a byproduct of the plants based on the predicted value. A method for forecasting includes determining a composite value of a characteristic in plants from a prior time period, correlating source data of plants to be gathered in the later time period with a predicted value of the characteristic in those plants, and determining a predicted composite value of the characteristic in the plants to be gathered in the later time period.

16 Claims, 6 Drawing Sheets

(51) Int. Cl.
  *G01N 33/03*  (2006.01)
  *G01N 21/17*  (2006.01)

(56) References Cited

OTHER PUBLICATIONS

Do et al., "Trends in Analytical Chemistry," Trends in Analytical Chemistry 66: 146-157 (2015).
Foss, "Best practice for calibration of NIR instruments with global models," accessible on the Internet at: https://www.fossanalytics.com/en/search?query=best%20practice (May 2008).
Galvez-Sola et al., "Rapid estimation of nutritional elements on citrus leaves by near infrared reflectance spectroscopy," Frontiers in Plant Science, 6(571): 1-8 (Jul. 2015).
Ismail, "Quick Determination of Actual Oil Content in Oil Palm Fruit Bunch Using Near Infrared (NIR) scanning spectrometer," A thesis submitted in partial fulfillment of the requirements for the award of the degree of Bachelor of Engineering (Chemical Engineering), Universiti Malaysia Pahang (Nov. 2010).
Jamshidi et al., "Analysis of citrus peel for non-destructive determination of fruit composition by reflectance Vis/NIR spectroscopy," XXXIV CIOSTA CIGR V Conference 2011, Vienna, Austria (Jun. 29, 2011).
Kasemsumran et al., "A Feasibility Study on Non-Destructive Determination of Oil Content in Palm Fruits by Visible—Near Infrared Spectroscopy," Journal of Near Infrared Spectroscopy, 20(6): 687-694 (2012) (Abstract).
Metrohm, "Manual—NIRS DS2500 Analyzer," accessible on the Internet at: https://www.metrohm.com/en-us/products-overview/spectroscopy/nirs%20lab%20analyzers/29220010?fromProductFinder=true (publicly available prior to filing of the instant application).
Miller et al., "Non-Destructive Brix Sensing of Florida Grapefruit and Honey Tangerine," Proc. Fla. State Hort. Soc., 115:56-60 (2002).
Mills, "Foss—NIR technology for routine analysis of food and agricultural products," accessible on the Internet at: https://www.fossanalytics.com/en/news-articles/technologies/nir-technology (Dec. 1, 2017).
Reddy et al., "Non-Destructive Quality Assessment of Citrus Fruits Using FT-Near-Infrared Spectroscopy," International Journal of Science, Environment and Technology, 5(4): 1850-1860 (2016).
Sánchez, "Citrus Internal Quality Predictions by NIR Spectroscopy," Tree and Forestry Science and Biotechnology, 2(Special Issue 1): 77-82 (2008).
Sánchez, "Using NIRS spectroscopy to predict postharvest quality," CAB Reviews: Perspectives in Agriculture, Veterinary Science, Nutrition and Natural Resources, 7(21): 1-14 (2012).
Schulz et al., "Application of near infrared spectroscopy for the quantification of quality parameters in selected vegetables and essential oil plants," J. Near Infrared Spectrosc., 6: A125-A130 (1998).
Shao et al., "Near-Infrared Spectroscopy for Classification of Oranges and Prediction of the Sugar Content," International Journal of Food Properties, 12: 644-658 (2009).
Steuer et al., "Classification and analysis of citrus oils by NIR spectroscopy," Food Chemistry, 72(1): 113-117 (2001) (Abstract).
Yasushi et al., "Development of a Mobile Grading Machine for Citrus Fruit," Engineering in Agriculture, Environment and Food, vol. 4, No. 1, pp. 7-11, Jan. 1, 2011.
International Search Report and Written Opinion dated Aug. 19, 2020 in PCT/US2020/020742.

TECHNOLOGIES FOR THE SELECTION AND PROCESSING OF PLANTS

BACKGROUND

Plants, like fruits and vegetables such as oranges, contain desirable "primary" products, such as juice for dietary consumption, that can be extracted through processing. The primary products of some plants, for example citrus fruits, have more desirable characteristics, such as brix, acidity, color, pH, bitterness, etc., than other plants. The plants may also contain other desirable byproducts, such as oils, that are useful on their own or in forming other end products. For example, citrus peel oil is an essential oil and valuable byproduct used in the flavor and fragrance industry that is extracted from oranges and other citrus fruits during the manufacture of fruit juices. The quantity and quality of primary products and byproducts in the plants can be affected by a number of different environmental factors and can vary across different varieties of the same plant. As an example, there are known differences between Hamlin oranges and Valencia oranges.

Identifying and understanding the quantity and quality of the contents of the plants, e.g., the primary products and the byproducts, such as total available oil (TAO), requires testing. Some methods include gathering the plant, and sending the gathered plant to a laboratory for destructive, "wet chemistry" testing where the plant is pulverized, blended with water, chemically extracting oil from an aliquot by distillation, and titrating the oil to determine the TAO. This process, however, is time consuming, expensive, and results in destruction of the plant rendering it unusable as an end product for sale. This presents challenges to the sourcing and processing of fruits.

This background provides some information believed to be of possible relevance to the present disclosure. No admission is intended, nor is such an admission to be inferred or construed, that any of the preceding information constitutes prior art against the present disclosure.

BRIEF DESCRIPTION OF THE DRAWINGS

The concepts described herein are illustrated by way of example and not by way of limitation in the accompanying figures. For simplicity and clarity of illustration, elements illustrated in the figures are not necessarily drawn to scale. Where considered appropriate, reference labels have been repeated among the figures to indicate corresponding or analogous elements.

DETAILED DESCRIPTION

As previously noted, plants contain various valuable primary products and byproducts. For ease of description, the disclosed embodiments are described in reference to fruits. Accordingly, when the description and drawings refer to fruits, one of skill will understand that such a reference is equally applicable to plants and that the described embodiments apply to any plant material, including all components thereof such as trees, bushes, roots, stalks, seeds, leaves, nuts, bark, fruits, and vegetables, and other attached/detached vegetation and material. In some aspects, the material is a plant that may be edible such as an edible fruit or vegetable. In certain aspects, the fruit may include, but is not limited to, fruits in the *Rutaceae* family, also commonly known as the citrus family, and may be exemplified by oranges, lemons, grapefruits, pomelos, limes, mandarins, clementines, tangerines, and grapefruits, and which may be referred to in this application as citrus fruits.

Fruit oil, such as the oil extracted from the peels of oranges, is a valuable byproduct from the processing of fruit. Some fruit can have more desirable quantity/quality of primary products, such as juice, and less desirable quantity/quality of byproducts. It can be beneficial to understand the specific contents of a fruit at the sourcing and processing stages in order to maximize the extraction of valuable primary products and byproducts from the fruit. In some embodiments, this includes adjusting an extraction process based on the determined contents of the fruit.

Some methods for identifying the quantity/quality of these primary products and byproducts in the fruit are destructive, leaving the fruit unusable for use in forming an end product, which is wasteful and costly. These testing methods are also time consuming (slowing down production) and expensive to conduct, and are used primarily to estimate an overall oil recovery post-processing. This can leave fruit processors at a disadvantage when sourcing and processing fruit, and provides no early read information to support primary product and/or byproduct recovery. Some fruit can have a low quality of juice, thereby de-valuing the cost of the fruit, but also contain a high quantity of oil. This can provide a value benefit by allowing high oil content fruit to be purchased at a lower relative cost for extraction of the valuable oil byproduct. Similarly, fruits with combinations of low primary product and low byproduct (and high primary product and high byproduct) may be identified, sourced, and processed with advantage. Due to the limitations of some testing methods, growers and sources of fruit are left unaware of the quality/quantity of contents in the fruit at the sourcing and processing stages of production. In some instances, growers receive a price for fruit that is based on the quality/quantity of primary product without material consideration of the value of byproduct(s) contained in that particular fruit. Consideration of the quantity of byproduct present in the fruit does not go further than what is known in general of the variety (e.g., that Valencia orange varieties have higher oil content than Hamlin orange varieties). In accordance with the present disclosure, Near-Infrared (NIR) scanning technology can provide rapid, non-destructive testing of fruit contents in a mobile platform that allows for maximization of value through the preferential sourcing and processing of fruit by understanding the quality/quantity of contents in the fruit at the sourcing and processing stages of production, including within a fruit variety and across fruit varieties.

Figure 1:
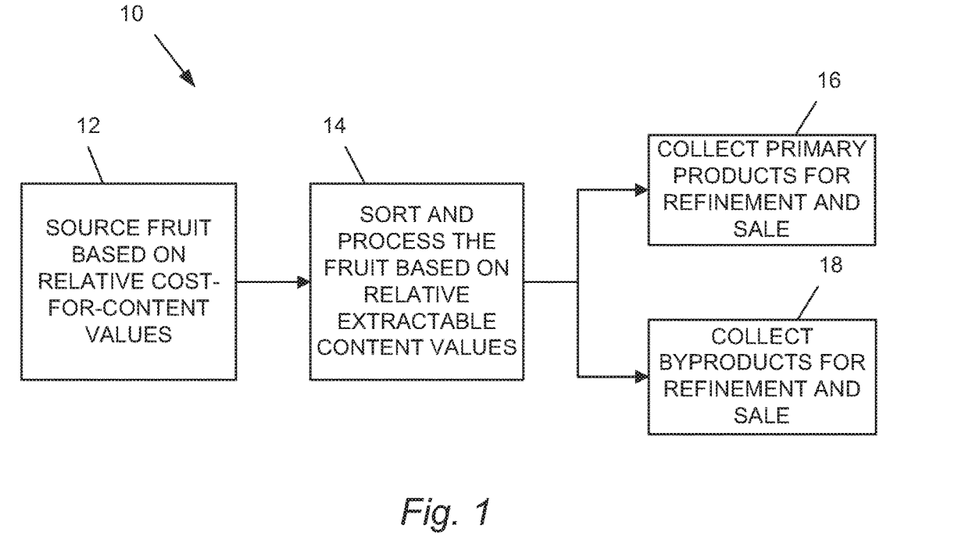
FIG. 1 is a simplified block diagram of at least one embodiment of a value-maximization method in accordance with the present disclosure for collecting primary products and byproducts from plants showing that the plants are sourced based on relative cost-for-content values, sorted and processed based on relative extractable content values, and the resulting primary products and byproducts collected for refinement and sale.

One embodiment of a value-maximization method 10 in accordance with the present disclosure for collecting primary products and byproducts from fruits, such as oranges, is shown in FIG. 1. The value-maximization method 10 includes a sourcing method 12 and a sorting and processing method 14 for collecting primary products 16 and collecting byproducts 18 from the fruit for later refinement and sale. The primary products can include, for example, juice from the inner body of the fruit, among other primary products. Desirable qualities of the primary products can include, for example, Brix (i.e., sugar content), acidity, color, pH, and bitterness, among other desirable qualities. These characteristics can also be used as indicators of the maturity and/or quality of the overall fruit. The byproducts can include, for example, oil (sometimes referred to as peel oil or essential oil) that is stored mainly in the peel of the fruit, among other desirable byproducts. Understanding the quantity of both the primary products and byproducts in the fruit can also be desirable.

Figure 2:
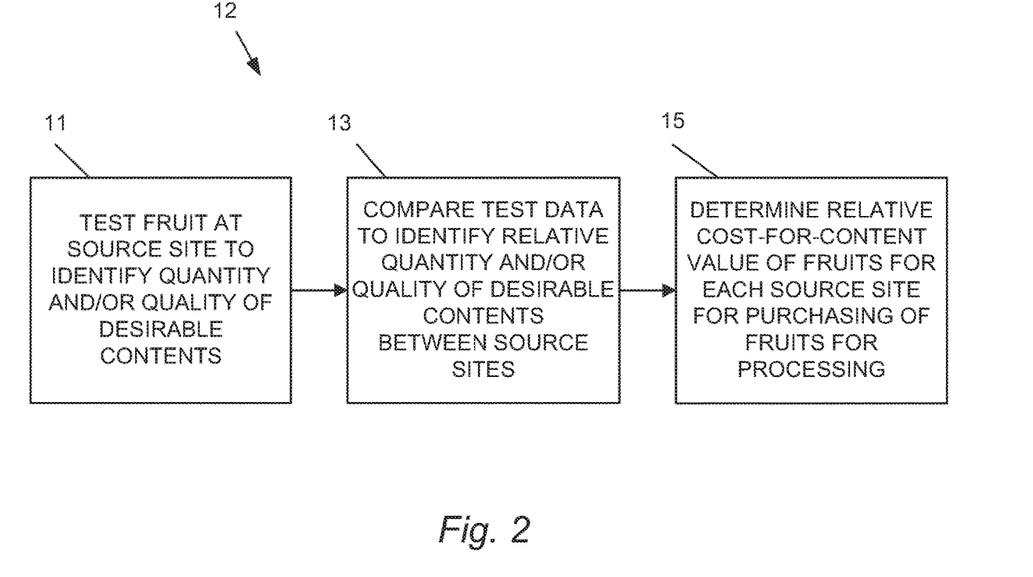
FIG. 2 is a simplified block diagram of at least one embodiment of a sourcing method in accordance with the present disclosure for sourcing plants showing that the plants at various source sites are tested, the test data is compared between source sites, and relative values determined for purchasing plants for processing.

One embodiment of the sourcing method 12 in accordance with the present disclosure for use in the value-maximization method 10 is shown in FIG. 2. The sourcing method 12 includes a testing step 11, a comparison step 13, and a determination step 15. The testing step 11 includes testing of fruit at a source site, such as where the fruit is grown, to identify the quantity and/or quality of desirable contents in the fruit. In some embodiments, the fruit can be tested to identify the quantity of oil contained in the fruit. In some embodiments, the fruit can be tested to identify the quantity of oil contained in the fruit and quality of juice contained in the fruit. In some embodiments, the testing step 11 is conducted at multiple times throughout a fruit's growth cycle. In some embodiments, the testing step 11 is conducted prior to purchasing of fruit for processing.

Figure 3:
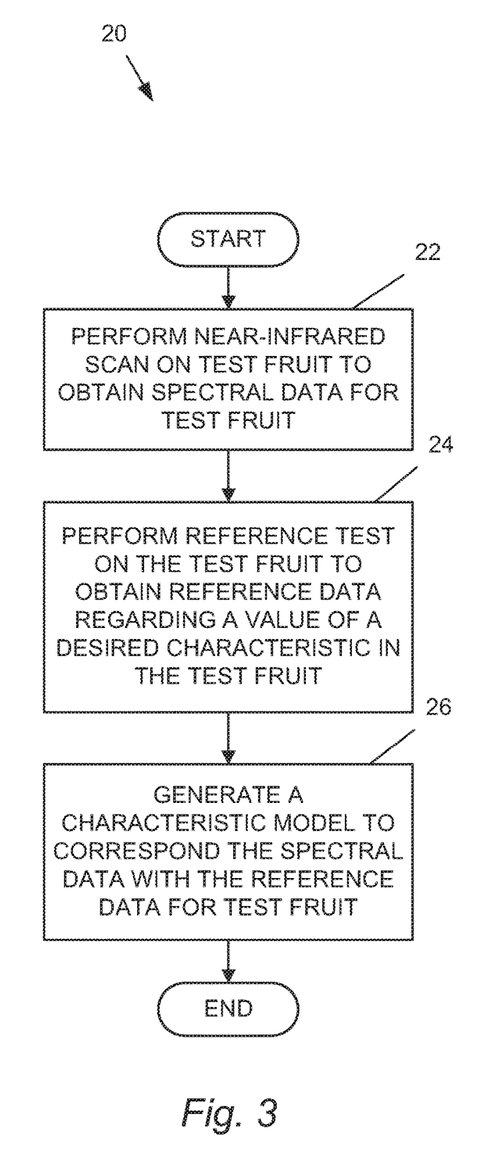
FIG. 3 is a simplified block diagram of at least one embodiment of a calibration method in accordance with the present disclosure for calibrating a near-infrared scanner for use in determining the contents of plants.

NIR scanning technology can be used in the testing of fruit and determining the quality/quantity of contents of the fruit. One embodiment of a calibration method 20 in accordance with the present disclosure for calibrating a near-infrared scanner for use in determining the contents of fruit is shown in FIG. 3. In the illustrative embodiment, one or more NIR scans are conducted on a test fruit to obtain spectral data for the test fruit in a scan step 22. In a reference step 24, a reference test, such as a destructive, wet chemistry test, is performed on the test fruit to obtain reference data regarding a value of a desired characteristic (e.g., quantity/quality of primary product and/or byproduct) in the test fruit. In a modeling step 26, a characteristic model is generated to correlate the spectral data with the reference data. In some embodiments, the characteristic model is generated with an algorithm, chemometrics, and/or other statistical principles. Later NIR scans on other fruit can then be evaluated against the characteristic model to determine the value of the desired characteristic in the other fruit of the same type (e.g., both fruits are oranges). In some embodiments, characteristic models are generated for different varieties of fruit (e.g., Hamlin and Valencia oranges).

Figure 4:
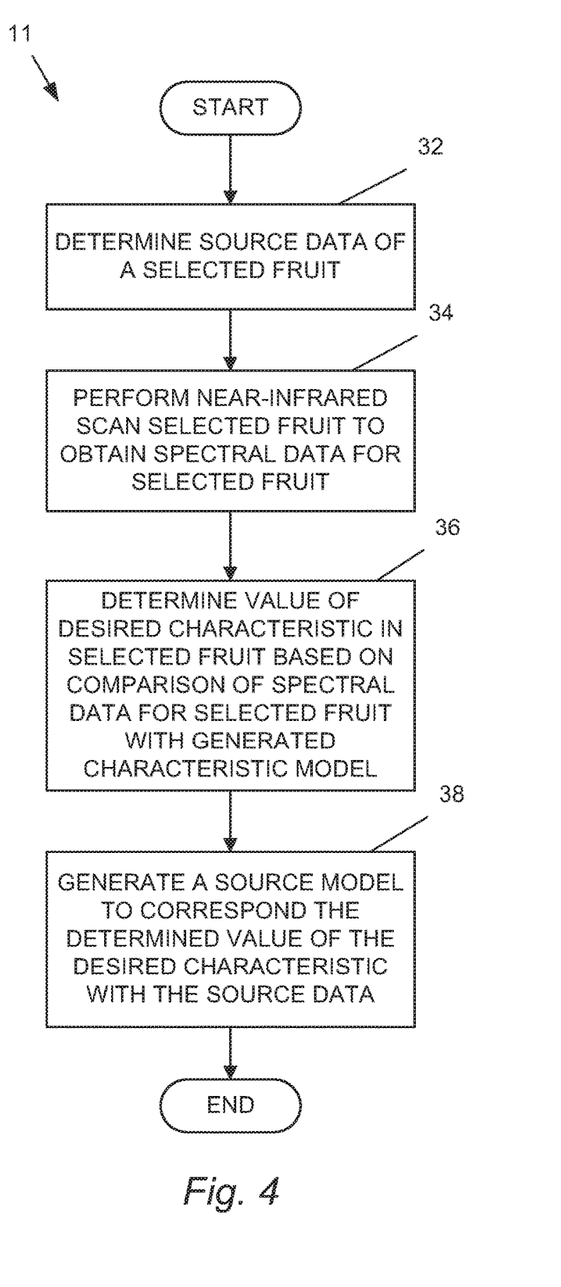
FIG. 4 is a simplified block diagram of at least one embodiment of a testing method in accordance with the present disclosure for generating a source model to correlate source data of plants with data regarding the contents of the plants.

In the illustrative embodiment, the testing step 11 is conducted at multiple source sites as suggested in FIG. 2. The source sites (sometimes referred to as groves or orchards) can be geographically separated from one another. The source sites can also have different environmental characteristics (such as soil composition, sunlight, humidity, health and maturity of the plant, etc.), and can produce different varieties of fruit (such as Hamlin oranges or Valencia oranges). The comparison step 13 of the sourcing method 12 compares the test data obtained in the testing step 11 from the various source sites to identify relative qualities/quantities of contents in the fruit at the various source sites. In some embodiments, the testing step 11 and/or the comparison step 13 can be completed within minutes, providing an advantage over other methods for determining the contents of fruit that require several hours or even days to complete In accordance with the present disclosure, the testing step 11 of the sourcing method 12 follows a testing method as shown in FIG. 4. In a determination step 32, source data for a selected fruit is determined. In some embodiments, the source data can include geolocation data, name of the grove, size of the grove, expected yield of the grove (i.e., amount of fruit harvested), environmental conditions, and other information related to the source site for the selected fruit being tested. In a scanning step 34, an NIR scan is conducted on the selected fruit to obtain spectral data for the selected fruit. In a comparison step 36, the spectral data is evaluated based on the generated characteristic model, as described herein, to determine a value of a desired characteristic of the selected fruit (e.g., quantity/quality of primary product and/or byproduct). In a modeling step 38, a source model is generated to correlate the determined value of the desired characteristic with the source data.

The source model can also include information for the fruit from multiple source sites using the testing method 11 for use in determining a relative cost-for-content value in the determination step 15 of the sourcing method 12 as suggested in FIG. 2. In some embodiments, the output of the determination step 15 is based on the output of the comparison step 13 and cost data provided by the source sites. In some embodiments, a relative price is estimated based on the output of the comparison step 13 for use in the determination step 15. Understanding of the cost-for-content value of the fruit allows a sourcer of fruit to purchase fruit for processing that minimizes the cost of producing valuable end products.

Figure 5:
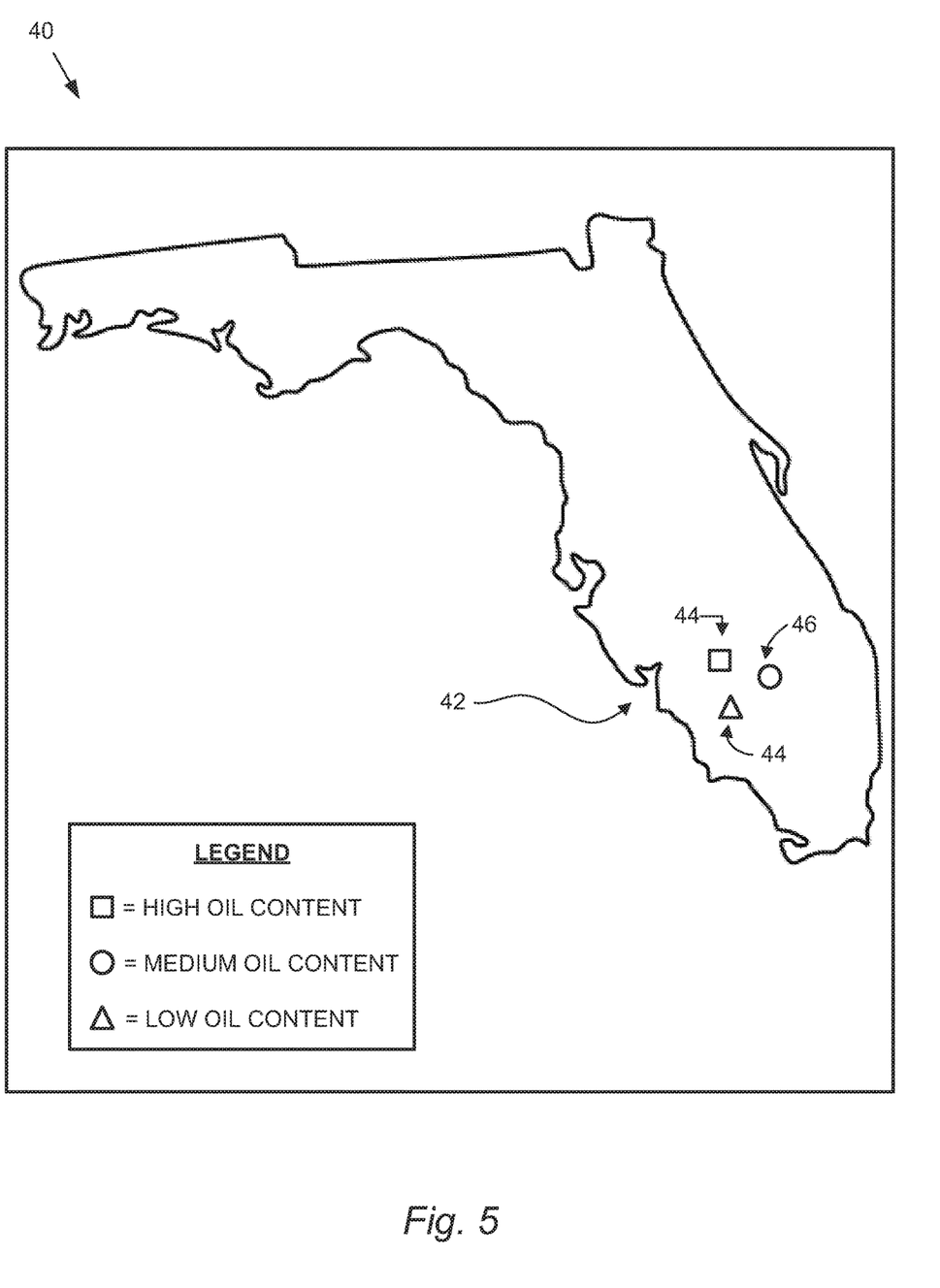
FIG. 5 is a diagrammatic view of a source map in accordance with the present disclosure showing that the source map visually represents a correlation between source data of plants and data regarding the contents of the plants.

In one illustrative embodiment, the source model generated from the testing method 11 can be used in generating a source map 40 as shown in FIG. 5. The source map 40 graphically represents the source site locations and information regarding the source sites. The source map 40 includes a graphical representation of a landmass 42, such as an outline of the State of Florida, and superimposed identifiers 44, 46, 48 at geolocations within the landmass 42. The identifiers 44, 46, 48 can correspond to data regarding desirable characteristics of the fruit at the source site, such as relative oil content. Other information can also be included and visible at the selection of a user. In some embodiments, weather data can be superimposed onto the source map 40 so that a user can determine potential effects on the fruit at the various source sites. For example, a hurricane may pass over certain source sites and have a predictable effect on the contents of the fruit at those source sites (e.g., lower oil content). In some embodiments, this information can then be used in adjusting the cost-for-value for the fruit and prior to selecting source sites for gathering fruit for processing.

Figure 6:
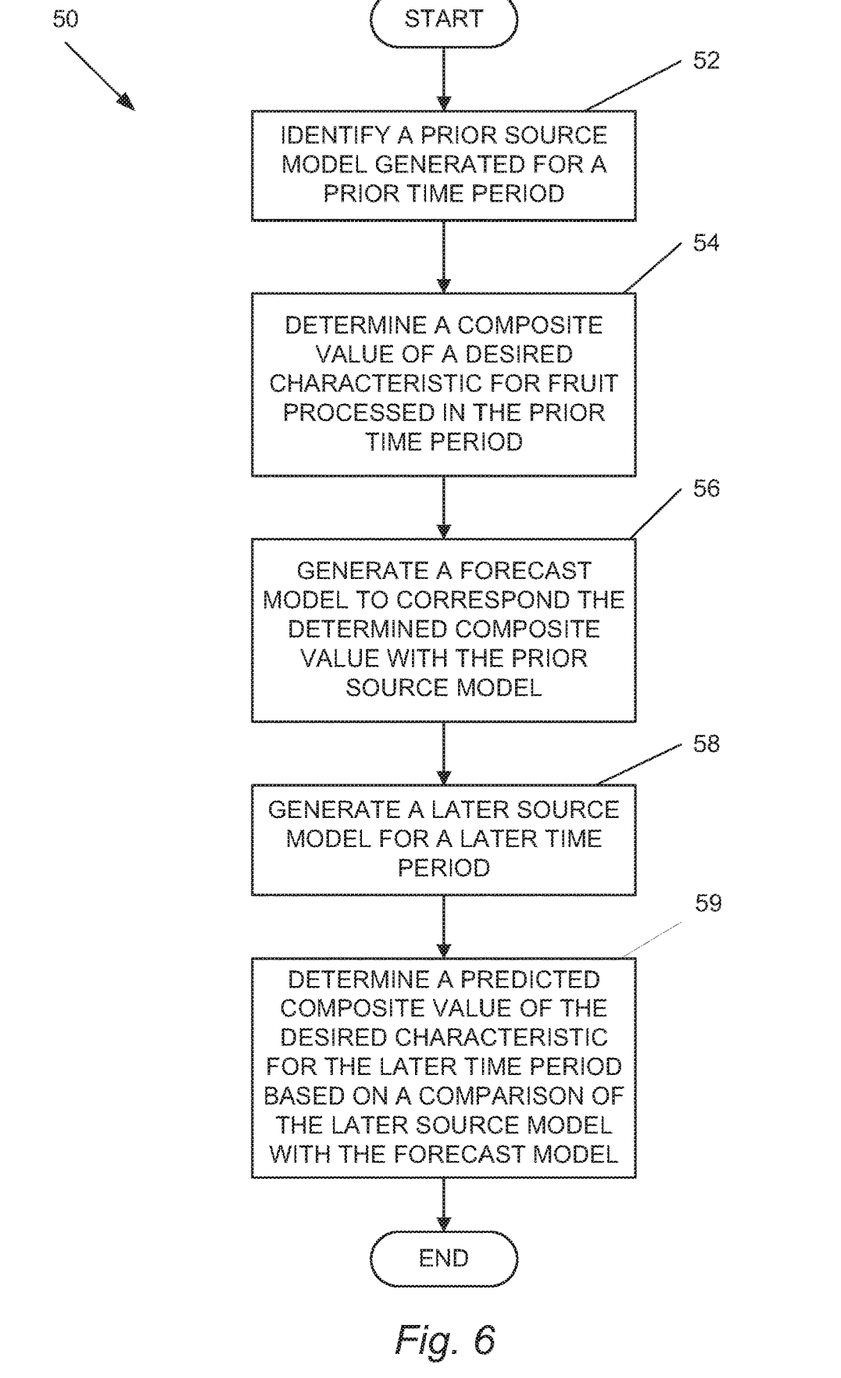
FIG. 6 is a simplified block diagram of at least one embodiment of a forecasting method in accordance with the present disclosure for determining a predicted value of the contents of plants.

One illustrative embodiment of a forecasting method 50 in accordance with the present disclosure for determining a predicted value of the contents of fruit is shown in FIG. 6. A source model, as described herein, for a prior time period (e.g., at the time of harvest from the prior year) is identified in an identification step 52. In a determination step 54, a composite value of a desired characteristic for fruit processed in the prior time period (e.g., total oil extracted) is determined. A forecast model is generated by correlating the determined composite value of the desired characteristic with the source model for the prior time period in a generating step 56. A source model for a later time period (e.g., pre-harvest of the current year) is generated in a generating step 58. In a determination step 59, a predicted composite value of the desired characteristic is determined by comparing the source model of the later time period with the forecast model. This predicted composite value can be beneficial in negotiating prices at the sourcing stage and expected collection of primary products and/or byproducts to recognize potential effects to expected profits from the sale of end products.

Figure 7:
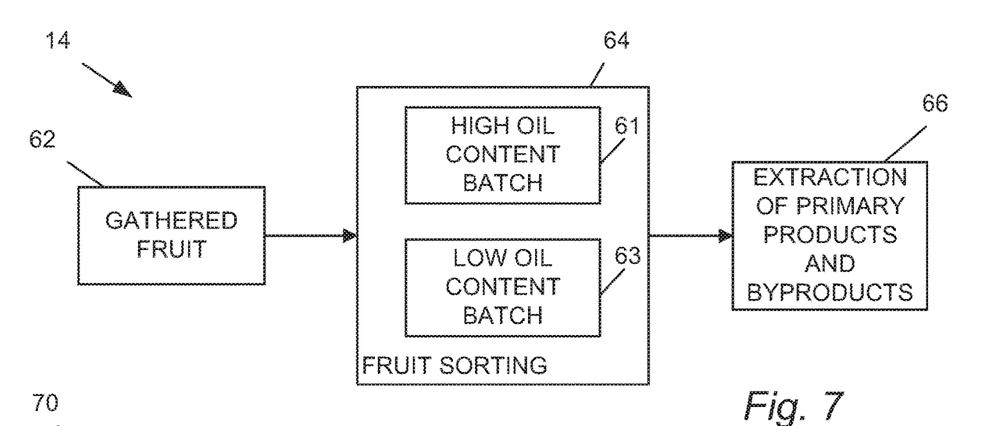
FIG. 7 is a simplified block diagram of at least one embodiment of a processing method in accordance with the present disclosure for maximizing a value of the extraction of the contents of the plants.

One embodiment of the sorting and processing method 14 in accordance with the present disclosure for use in the value-maximization method 10 is shown in FIG. 7. In the illustrative embodiment, fruit gathered during harvest is brought to a processing facility in a gathering step 62. Sorting of the fruit occurs in a sorting step 64 based on the determined extractable contents of the gathered fruit. In some embodiments, the extractable contents are known from the pre-determined source model, as described herein, and the fruit from each source is gathered in identifiable bins for sorting in sorting step 64. In some embodiments, a relative amount of oil in the fruit is used to sort the fruit into different batches 61, 63 for processing. In some embodiments, the fruit with the highest oil content is sorted into batch 61 and provided to equipment useful in extracting high oil content byproducts in an extraction process 66 while low oil content fruit is sorted into batch 63 for processing on other equipment useful in extracting primary products, such as juice, in the extraction process 66. It should be understood that batches 61, 63 are merely representative, and more or less batches can be used and be based on other desirable characteristics of the fruit.

Figure 8:
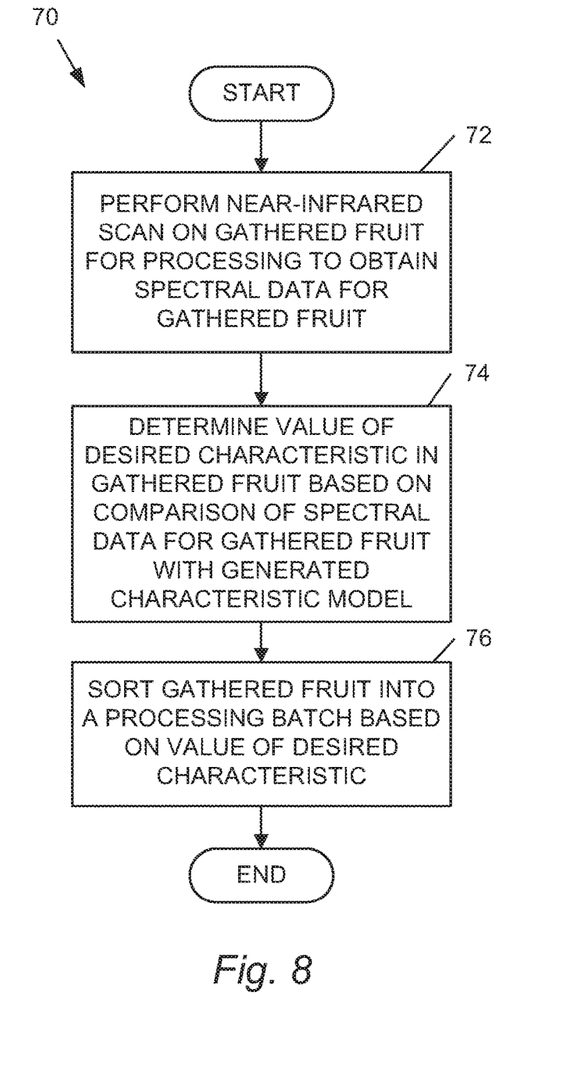
FIG. 8 is a simplified block diagram of at least one embodiment of a testing method in accordance with the present disclosure for identifying the extractable contents of plants and sorting the plants by the relative value of the extractable contents.

One embodiment of a testing method 70 in accordance with the present disclosure for identifying the extractable contents of fruit and sorting the fruit by the relative value of the extractable contents is shown in FIG. 8. A rapid, non-destructive NIR scan is performed on the gathered fruit to obtain spectral data for the gathered fruit in a scanning step 72. The spectral data is evaluated based on a generated characteristic model, as described herein, to determine the value of the desired characteristic (e.g., quantity/quality of extractable contents) in a determination step 74. In a sorting step 76, the gathered fruit is sorted based on the relative value of the desired characteristic.

Figure 9:
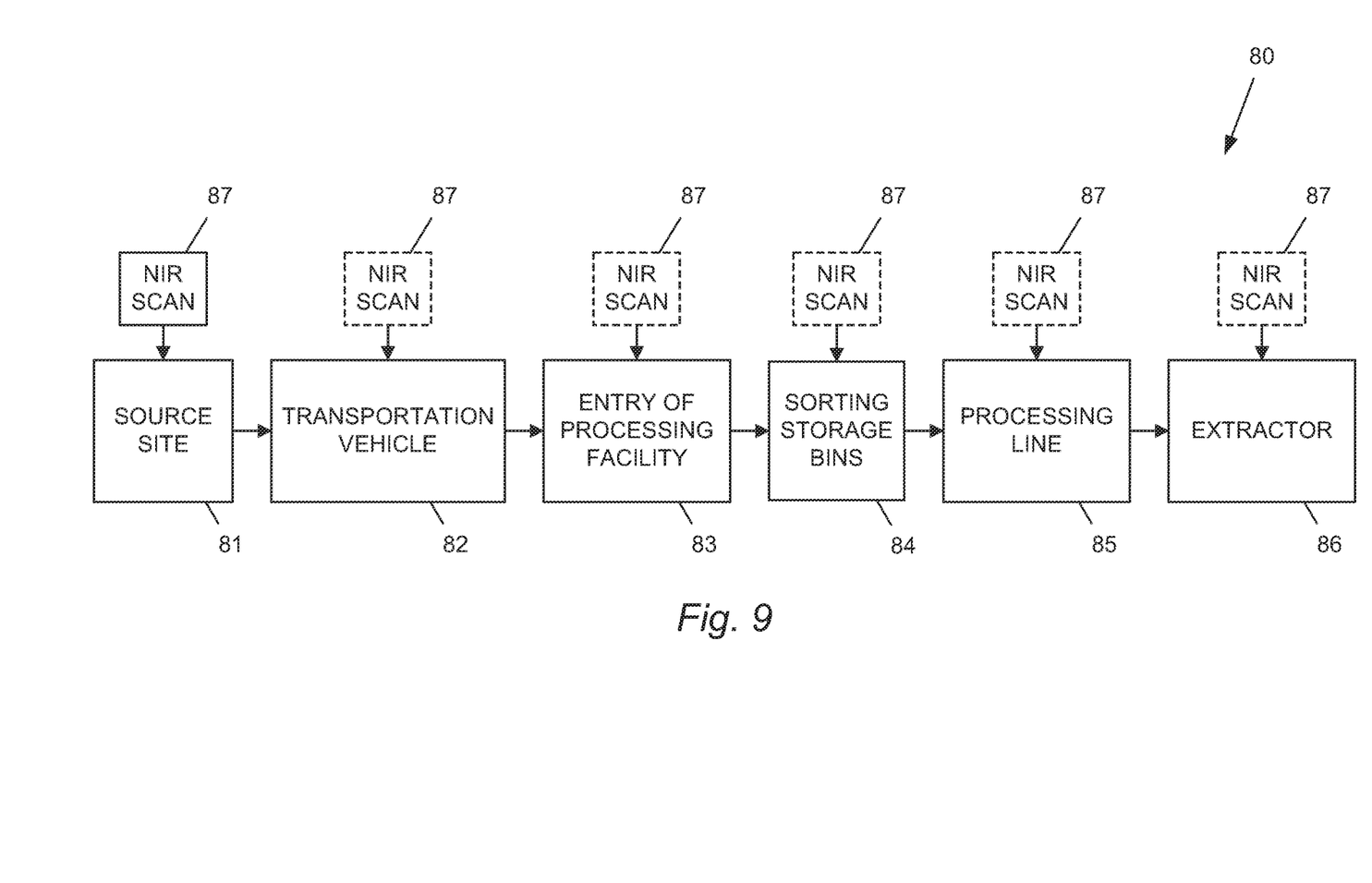
FIG. 9 is a simplified block diagram of at least one embodiment of a processing method in accordance with the present disclosure for maximizing a value of the extraction of the contents of the plants.

One embodiment of a processing method 80 in accordance with the present disclosure is shown in FIG. 9. In the illustrative embodiment, fruits are gathered at a source site 81 and deposited into a transportation vehicle 82. The transportation vehicle 82 travels from the source site 81 to a processing facility 83 where the gathered fruit are deposited into sorting storage bins 84. The gathered fruit are sorted based on their extractable contents and sent to processing lines 85 for clearing away unwanted matter (e.g., branches, leaves, etc.) and cleaning the fruit prior to extraction. Conveyors of the processing lines 85 lead to extractors 86 for extracting the primary products and/or byproducts from the gathered fruit. One or more NIR scans 87 can be taken throughout the processing method 80 for determining the amount and/or quality of extractable contents of the fruit. For example, as discussed herein, the fruit can be NIR scanned 87 at the source site 81 for advantaged sourcing of the fruit. In some embodiments, the NIR scan 87 at the source site 81 is used to extrapolate the amount and/or quality of extractable contents of fruit at the source site 81 (or individual "blocks" of the source site 81). In some embodiments, an NIR scan 87 as disclosed herein can be conducted during or after the fruit has been deposited onto the transportation vehicle 82. The NIR scan 87 at the transportation vehicle 82 can be used to extrapolate the amount and/or quality of extractable contents of fruit on the transportation vehicle 82. In some embodiments, an NIR scan 87 as disclosed herein can be conducted at the entry or within the processing facility 83 before the fruit is removed from the transportation vehicle 82. In some embodiments, an NIR scan 87 as disclosed herein can be conducted before sorting of the fruit into various sorting storage bins 84. The NIR scan 87 before sorting can be used to extrapolate the amount and/or quality of extractable contents of fruit in each sorting storage bin 84. In some embodiments, an NIR scan 87 as disclosed herein can be conducted before or during movement of the fruit from the sorting storage bins to the processing lines 85. The NIR scan 87 on the processing lines 85 can be used to extrapolate the amount and/or quality of extractable contents of fruit traveling on each processing line 85. In some embodiments, an NIR scan 87 as disclosed herein is conducted shortly before the fruit reaches the extractor 86. In some embodiments, an NIR scan 87 as disclosed herein is conducted as the fruit reaches the extractor 86 and/or during extraction in the extractor 86. In some embodiments, the NIR scan 87 at the extractor 86 can be used to determine when extraction is complete. The various NIR scans 87 allow for advantaged processing of the fruit and extraction of the contents thereof with more clarity. In some embodiments, an NIR scan is conducted on each fruit for maximizing the extraction processing thereof.

Understanding the contents of fruit can provide for advantaged processing of the fruit. In some embodiments, operation of primary product and/or byproduct extraction equipment can be adjusted based on the determined characteristics of the fruit. For example, a Brown Oil Extractor (BOE), commercially available from Brown International Corporation, LLC, uses a plurality of spiked rollers to extract oil from oranges. An adjustable speed differential between adjacent rollers controls the amount of work applied to the oranges for extracting the oil (e.g., more work extracts more oil), but can also affect juice quality by introducing potentially bitter flavors into the juice from the oil. The processing time can also affect the amount of oil extracted from the oranges (e.g., more time extracts more oil). In some embodiments, the feed rate of oranges into the BOE affects the feed rate of the oranges through the BOE, and the processing time can be controlled with a slower or faster feed rate. Some oranges with higher oil content can exhibit a higher rate of extraction under the same processing conditions as oranges with lower oil content, allowing higher oil content oranges to be processed at a higher speed while extracting the same or more oil than a low oil content orange processed at a slower speed. In some embodiments, oranges with high oil content and low juice quality (i.e., low brix) can be processed through a BOE at a faster rate and with a greater speed differential between adjacent rollers (i.e., more work applied to the oranges). In some embodiments, oranges with high oil content and high juice quality (i.e., high brix) can be processed through a BOE at a faster rate and with a lesser speed differential between adjacent rollers (i.e., less work applied to the oranges). In some embodiments, oranges with low oil content and low juice quality can be processed through a BOE at a slower rate and with a greater speed differential between adjacent rollers. In some embodiments, oranges with low oil content and high juice quality can be processed through a BOE at a slower rate and a lesser speed differential between adjacent rollers. Other extraction processes can also be adjusted according to the characteristics of those processes based on the determined extractable contents as described herein. In some embodiments, the primary products, such as juice, are extracted from the fruits after the oil has been extracted.

In illustrative embodiments, the methods and procedures described herein are useful in determining the contents of fruits, and in particular citrus fruits such as oranges, lemons, limes, tangerines, grapefruits, and mandarins, among others.

In illustrative embodiments, a sourcer or processor of fruit can quickly determine TAO with NIR scanning technology without destroying the whole intact fruit and with high accuracy and precision. The fruit can subsequently and advantageously be processed with advanced and prior knowledge of the TAO. The ability to map oil to the source during annual crop pre-harvest operations allows a sourcer the ability to use the knowledge to advantageously select fruit with higher intrinsic concentrations of TAO. A processor can also selectively sort fruit using prior oil mapping knowledge to increase the recovery of the oil extraction process from whole fruit prior to juicing. The testing information also enables early knowledge of expected oil, by several weeks, that will be recovered from fruit relative to prior seasons. This information can be used to generate a forecast prediction to guide sales strategy and arbitrage opportunity for byproduct peel oil, and storage capacity for advantaged sale.

While the concepts of the present disclosure are susceptible to various modifications and alternative forms, specific embodiments thereof have been shown by way of example in the drawings and will be described herein in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

References in the specification to "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. Additionally, it should be appreciated that items included in a list in the form of "at least one A, B, and C" can mean (A); (B); (C); (A and B); (A and C); (B and C); or (A, B, and C). Similarly, items listed in the form of "at least one of A, B, or C" can mean (A); (B); (C); (A and B); (A and C); (B and C); or (A, B, and C).

The disclosed embodiments may be implemented, in some cases, in hardware, firmware, software, or any combination thereof. The disclosed embodiments may also be implemented as instructions carried by or stored on a transitory or non-transitory machine-readable (e.g., computer-readable) storage medium, which may be read and executed by one or more processors. A machine-readable storage medium may be embodied as any storage device, mechanism, or other physical structure for storing or transmitting information in a form readable by a machine (e.g., a volatile or non-volatile memory, a media disc, or other media device).

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures. Additionally, the inclusion of a structural or method feature in a particular figure is not meant to imply that such feature is required in all embodiments and, in some embodiments, may not be included or may be combined with other features.

The invention claimed is:

1. A method for sourcing plants, the method comprising:
performing a nondestructive near-infrared (NIR) scan on a first selected plant at a first source site where the first selected plant is grown;
obtaining a first set of spectral data from the NIR scan of the first selected plant;
performing a nondestructive NIR scan on a second selected plant at a second source site where the second selected plant is grown;
obtaining a second set of spectral data from the NIR scan of the second selected plant;
identifying a characteristic model correlating NIR spectral data to a value of a characteristic present in the first and second selected plant;
determining a predicted value of the characteristic for the first and second selected plants based on evaluation of the first and second sets of spectral data against the characteristic model;
determining source data correlating the first selected plant with the first source site and the second selected plant with the second source site;
generating a source model correlating the source data with the predicted values of the characteristics for the first and second selected plants; and
utilizing the source model for at least one of a purchasing decision, a processing decision, and financial forecasting related to the first and second source sites.

2. The method of claim 1, wherein the characteristic is at least one of an amount of available oil in the plant; brix; acidity; color; pH; and bitterness.

3. The method of claim 1, wherein the first set of spectral data is representative of all plants at the first source site and the second set of spectral data is representative of all plants at the second source site.

4. The method of claim 3, further comprising:
identifying cost data for the first and second selected plants;
determining a cost-for-content value for each of the first and second selected plants by comparing the cost data with the source model; and
comparing the cost-for-content values of the first and second selected plants.

5. The method of claim 4, further comprising determining whether to purchase plants from one or both of the first source site and second source site based on the cost-for-content values of the first and second selected plants.

6. The method of claim 1, further comprising generating a source map graphically representing a correlation between the source data and predicted value of the characteristic relative to a graphical representation of a landmass.

7. The method of claim 1, wherein the source data for each of the first and second selected plants includes at least one of:
a geolocation for the corresponding first or second source site;
identifying information for the corresponding first or second source site;
a land area of the corresponding first or second source site;
an expected yield of the corresponding first or second source site; and
environmental conditions of the corresponding first or second source site.

8. The method of claim 1, further comprising generating the characteristic model, wherein generating the characteristic model comprises:
performing nondestructive NIR scans on a plurality of test plants of the same type as the first and second selected plants;
obtaining spectral data from the NIR scans of the test plants;
performing reference tests on the test plants;
obtaining reference data of a value of the characteristic in the test plants from the reference tests; and
correlating the spectral data from the NIR scans of the test plants with the reference data.

9. A method of sorting and processing plants, the method comprising:
gathering plants for processing;
determining a predicted value of a characteristic in the plants;
sorting the plants into a first batch and a second batch based on a relative predicted value of the characteristic in the plants, the first batch including plants having a relatively higher predicted value of the characteristic than plants in the second batch;
determining a process to recover a primary product and/or a byproduct of the plants in the first batch based on the predicted value of the characteristic in the plants in the first batch; and
determining a process to recover a primary product and/or a byproduct of the plants in the second batch based on the predicted value of the characteristic in the plants in the second batch
wherein determining a predicted value of the characteristic in the plants comprises:
performing a nondestructive near-infrared (NIR) scan on a selected plant from the plants;
obtaining spectral data from the NIR scan of the selected plant;
identifying a characteristic model correlating NIR spectral data to a value of a characteristic of plants of the same type as the selected plant; and
evaluating the spectral data against the characteristic model.

10. The method of claim 9, wherein the characteristic is at least one of: an amount of available oil in the plant; brix; acidity; color; pH; and bitterness.

11. The method of claim 9, further comprising generating the characteristic model, wherein generating the characteristic model comprises:
performing nondestructive NIR scans on a plurality of test plants of the same type as the selected plant;
obtaining spectral data from the NIR scans of the test plants;
performing reference tests on the test plants;
obtaining reference data of a value of the characteristic in the test plants from the reference tests; and
correlating the spectral data from the NIR scans of the test plants with the reference data.

12. The method of claim 9, wherein the primary product is juice and the byproduct is oil.

13. A method for forecasting, the method comprising:
identifying a source model for a prior time period, the source model for the prior time period correlating source data of plants gathered in the prior time period with a predicted value of a characteristic in the plants gathered in the prior time period;
determining a composite value of the characteristic in the plants in the prior time period;
generating a forecast model correlating the composite value with the source model for the prior time period;
generating a source model for a later time period, the source model for the later time period correlating source data of plants to be gathered in the later time period with a predicted value of the characteristic in the plants to be gathered in the later time period; and
determining a predicted composite value of the characteristic in the plants to be gathered in the later time period by comparing the source model for the later time period with the forecast model.

14. The method of claim 13, wherein the characteristic is at least one of: an amount of available oil in the plant; brix; acidity; color; pH; and bitterness.

15. The method of claim 13, wherein generating the source model for a later time period comprises:
performing nondestructive near-infrared (NIR) scans on selected plants from the plants to be gathered in the later time period;
obtaining spectral data from the NIR scans of the selected plants;
identifying a characteristic model correlating NIR spectral data to a value of the characteristic of plants of the same type as the selected plants;
determining a predicted value of the characteristic for the selected plants based on an evaluation of the spectral data against the characteristic model;
determining source data correlating the selected plants with source sites where the plants to be gathered is grown; and
correlating the source data with the predicted value of the characteristic for the selected plants.

16. The method of claim 15, further comprising generating the characteristic model, wherein generating the characteristic model comprises:
- performing nondestructive NIR scans on a plurality of test plants of the same type as the selected plants;
- obtaining spectral data from the NIR scans of the test plants;
- performing reference tests on the test plants;
- obtaining reference data of a value of the characteristic in the test plants from the reference tests; and
- correlating the spectral data from the NIR scans of the test plants with the reference data.

\* \* \* \* \*